United States Patent
Kondo

(10) Patent No.: US 12,083,298 B2
(45) Date of Patent: Sep. 10, 2024

(54) GUIDE WIRE

(71) Applicant: TERUMO KABUSHIKI KAISHA, Tokyo (JP)

(72) Inventor: Shinji Kondo, Ebina (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 451 days.

(21) Appl. No.: 17/464,930

(22) Filed: Sep. 2, 2021

(65) Prior Publication Data
US 2021/0393926 A1 Dec. 23, 2021

Related U.S. Application Data

(63) Continuation of application No. PCT/JP2020/005539, filed on Feb. 13, 2020.

(30) Foreign Application Priority Data

Mar. 4, 2019 (JP) ................. 2019-038774

(51) Int. Cl.
*A61M 25/09* (2006.01)
*A61B 17/34* (2006.01)
*A61M 29/00* (2006.01)

(52) U.S. Cl.
CPC ......... *A61M 25/09* (2013.01); *A61B 17/3478* (2013.01); *A61M 29/00* (2013.01);
(Continued)

(58) Field of Classification Search
CPC .................. A61M 25/09; A61M 29/00; A61M 2025/09091; A61M 2025/09183;
(Continued)

(56) References Cited

U.S. PATENT DOCUMENTS 8,992,556 B2 3/2015 Chanduszko et al.
2007/0219464 A1 9/2007 Davis et al.
(Continued)

FOREIGN PATENT DOCUMENTS

CN 101098728 A 1/2008
CN 105120939 A 12/2015
(Continued)

OTHER PUBLICATIONS

International Search Report (PCT/ISA/210) with translation and Written Opinion (PCT/ISA/237) mailed on Apr. 21, 2020, by the Japanese Patent Office as the International Searching Authority for International Application No. PCT/JP2020/005539.
(Continued)

*Primary Examiner* — Richard G Louis
(74) *Attorney, Agent, or Firm* — BUCHANAN INGERSOLL & ROONEY PC

(57) ABSTRACT

A guide wire for guiding a dilator to be inserted into a living body includes: a flexible elongated shaft portion; a puncture portion at a distal end portion of the shaft portion to form a hole in biological tissue; and an elastically deformable cover portion covering the puncture portion. The cover portion includes a sparse pitch portion that has a wire member wound in a spiral shape and axially contractible, and a distal end cover located on a distal end side of the sparse pitch portion and covering at least a part of the puncture portion. The puncture portion includes a first contact portion. The distal end cover includes a second contact portion configured to contact the first contact portion from a proximal end side, so that relative axial movement of the first and second contact portions is restricted by the first contact portion contacting the second contact portion.

18 Claims, 5 Drawing Sheets

(52) U.S. Cl.
CPC ............. *A61M 2025/09091* (2013.01); *A61M 2025/09183* (2013.01)

(58) Field of Classification Search
CPC ...... A61B 17/3478; A61B 2017/00247; A61B 2017/22044; A61B 17/3421; A61B 17/3494; A61B 17/3496; A61B 2090/08021; A61B 17/3401
See application file for complete search history.

(56) References Cited

U.S. PATENT DOCUMENTS

| | | |
|---|---|---|
| 2009/0198153 A1 | 8/2009 | Shriver |
| 2014/0371676 A1* | 12/2014 | Leeflang ............ A61B 17/3423 604/164.1 |
| 2015/0289901 A1 | 10/2015 | Khan et al. |

FOREIGN PATENT DOCUMENTS

| | | |
|---|---|---|
| EP | 1 872 819 A1 | 1/2008 |
| EP | 2 990 070 A1 | 3/2016 |
| EP | 3 603 727 A1 | 2/2020 |
| JP | 2011-147551 A | 8/2011 |
| WO | 2014/182969 A1 | 11/2014 |
| WO | 2018181520 A1 | 10/2018 |

OTHER PUBLICATIONS

Office Action (The First Office Action) issued Mar. 1, 2023, by the National Intellectual Property Administration, P. R. China in corresponding Chinese Patent Application No. 202080008912.7 and an English translation of the Office Action. (11 pages).

English Translations of the International Search Report (Form PCT/ISA/210) and the Written Opinion of the International Searching Authority (Form PCT/ISA/237) issued Apr. 21, 2020, by the Japanese Patent Office in corresponding International Application No. PCT/JP2020/005539. (6 pages).

The extended European Search Report issued Feb. 7, 2022, by the European Patent Office in corresponding European Patent Application No. 20766463.2-1113. (50 pages).

* cited by examiner

FIG. 4A
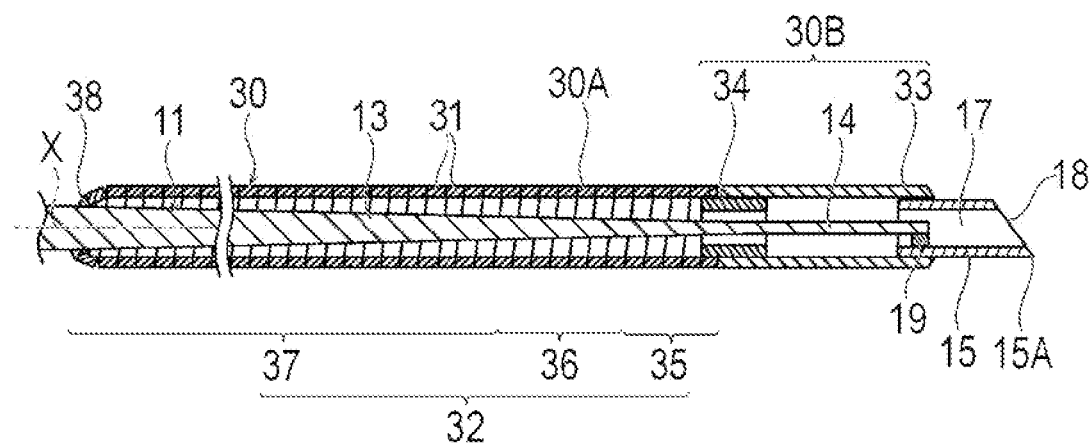
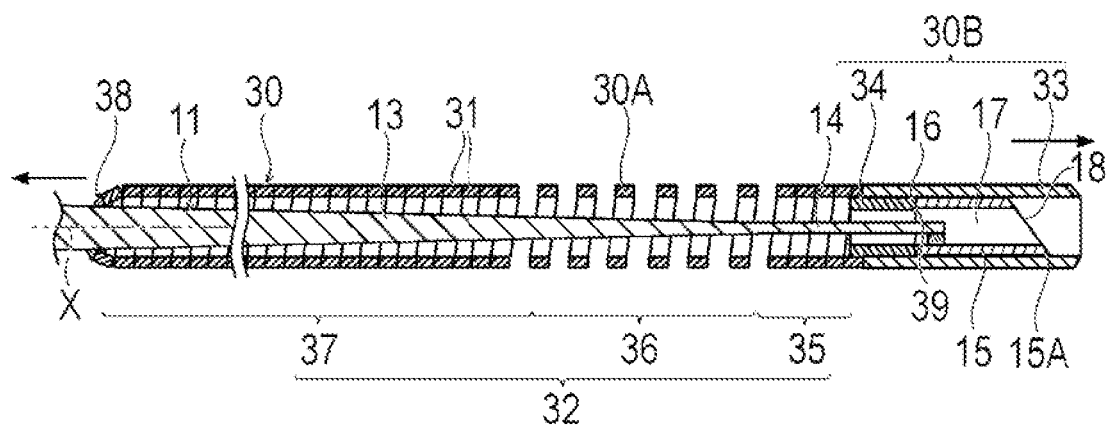
FIG. 4B

GUIDE WIRE

CROSS-REFERENCES TO RELATED APPLICATIONS

This application is a continuation of International Patent Application No. PCT/JP2020/005539 filed on Feb. 13, 2020, which claims priority to Japanese Patent Application No. 2019-038774 filed on Mar. 4, 2019, the entire content of both of which is incorporated herein by reference.

FIELD OF THE INVENTION

This disclosure generally relates to a guide wire for puncturing a biological tissue.

BACKGROUND DISCUSSION

A heart repeatedly contracts and expands at an appropriate timing by current flowing through myocardial tissue called a stimulation conduction system, and circulates blood. When generation or transmission of an electric signal flowing through the stimulation conduction system is not normal, contraction or expansion cannot be performed at the appropriate timing, and arrhythmia occurs.

As a method of treating arrhythmia, a method is known in which a conduction path of a signal that causes the arrhythmia is ablated and blocked by heating or cooling. As a device for performing the treatment method, there is known a device that can be percutaneously inserted to a left atrium and ablate a conduction path of a signal located at a pulmonary vein opening. Such an ablation device is widely used since the device is minimally invasive and highly effective.

Ablation performed in the left atrium requires a technique called an interatrial septum puncture (Brockenbrough method) in which a needle is inserted into a thin partition wall called a foramen ovalis of an interatrial septum from a right atrium to make a hole leading from the right atrium to the left atrium. A transseptal needle, which is a device for performing the interatrial septum puncture, includes a mechanical needle and a radio frequency needle. The mechanical needle becomes the mainstream due to low cost.

The mechanical needle performs puncture using a sharp needle. When the mechanical needle is used, a risk of erroneous puncture occurs due to excessive pressing of the needle. If the needle is erroneously punctured, serious complications called cardiac tamponade (a state in which blood accumulates between the pericardium and the cardiac muscle, which causes heart failure) may occur. On the other hand, the radio frequency needle is a method of passing through the interatrial septum by outputting high frequency energy supplied from a console which is a separately provided device. Therefore, the radio frequency needle does not have a risk of erroneous puncture, but is expensive and requires a console.

For example, U.S. Pat. No. 8,992,556 discloses a device in which an inner needle, which is the mechanical needle, is disposed inside a tubular outer needle. A distal end of the inner needle is bent so as to face a proximal end side. The distal end of the inner needle is accommodated in the outer needle in a linearly stretched state. The inner needle protrudes from the outer needle to form a hole in the interatrial septum from the right atrium side. After reaching the left atrium, the inner needle bends and faces the proximal end side. In view of this, the device disclosed in PTL 1 prevents the occurrence of the erroneous puncture due to the inner needle.

SUMMARY

The inner needle of the device disclosed in U.S. Pat. No. 8,992,556 is bent and faces the proximal end side after puncturing, but is not accommodated in another member. Therefore, in this device, the risk of erroneous puncture due to the inner needle remains. The inner needle is always exposed in the outer needle. Therefore, in a process of inserting the inner needle into the outer needle and transporting the inner needle to the interatrial septum, an inner side may damage the outer needle or a distal end portion of the inner needle may be damaged. A device that punctures a biological tissue is required to have high safety.

The guide wire disclosed here can prevent erroneous puncture by a puncture portion that performs puncture and can obtain high safety.

A guide wire according to this disclosure for achieving the above object is a guide wire for guiding a tubular elongated body to be inserted into a living body. The guide wire includes: an elongated shaft portion that has flexibility; a puncture portion that is disposed at a distal end portion of the shaft portion and forms a hole in a biological tissue; and a cover portion that is elastically deformable and covers the puncture portion. The cover portion includes a sparse pitch that has a wire member wound in a spiral shape and is contractible along a central axis of winding, and a distal end cover that is located on a distal end side of the sparse pitch and is capable of covering at least a part of the puncture portion. The shaft portion or the puncture portion includes a first contact portion. The distal end cover includes a second contact portion located on a proximal end side with respect to the first contact portion, and relative movement of the first contact portion and the second contact portion in an axial direction is restricted by the first contact portion coming into contact with the second contact portion.

In the guide wire constituted as described above, since the cover portion covers the puncture portion, erroneous puncture by the puncture portion is prevented, and high safety is obtained. In addition, since the first contact portion comes into contact with the second contact portion, relative movement of the first contact portion and the second contact portion in an axial direction is restricted, and extension of the cover portion is restricted.

According to another aspect, a guide wire for guiding a dilator to be inserted into a living body comprises a flexible elongated shaft portion that includes a distal end portion, a puncture portion fixed to the distal end portion of the elongated shaft portion so that the puncture portion moves together with the elongated shaft portion, and a cover portion. The puncture portion includes a distal end at which is located a sharp needle portion configured to puncture biological tissue in the living body to form a hole in the biological tissue. The cover portion is comprised of a sparse pitch portion and a distal end cover, with the distal end cover being positioned distal of the sparse pitch portion, and the sparse pitch portion being defined by a wire member that is spirally wound around a central axis of winding so that the wire member includes axially adjacent windings of the wire member. The axially adjacent windings of the wire member in the sparse pitch portion are axially spaced apart from one another so a gap exists between the axially adjacent windings allowing the sparse pitch portion to be axially contractible along the central axis of winding. The distal end cover covers at least a part of the puncture portion before a force is applied to the guide wire causing the sparse pitch portion to axially contract along the central axis of winding. A first contact portion is fixed to the shaft portion or the puncture portion, and a second contact portion is on the distal end cover and is positioned proximal of the first contact portion. The first contact portion and the second contact portion are configured to move from respective positions in which the first contact portion and the second contact portion are spaced from one another to positions in which the first contact portion and the second contact portion contact one another to restrict relative axial movement of the first contact portion and the second contact portion.

A further aspect of the disclosure involves a guide wire in combination with a sheath assembly, with the guide wire being configured to guide a part of the sheath assembly that is configured to be inserted into a living body. The guide wire comprises: a flexible elongated shaft portion that includes a distal end portion; a puncture portion fixed to the distal end portion of the elongated shaft portion so that the puncture portion moves together with the elongated shaft portion, and a cover portion. The puncture portion includes a distal end at which is located a sharp needle portion configured to puncture the biological tissue in the living body to form a hole in the biological tissue. The cover portion is comprised of a sparse pitch portion and a distal end cover, with the distal end cover positioned distal of the sparse pitch portion, and the sparse pitch portion being defined by a plurality of axially adjacent windings that are axially spaced-apart from one another so the sparse pitch portion is axially contractible to reduce spacing between the axially adjacent windings that are axially spaced-apart. The distal end cover covers at least a part of the puncture portion before a force is applied to the guide wire causing the sparse pitch portion to axially contract. A first contact portion is fixed to the shaft portion or the puncture portion, a second contact portion is on the distal end cover and is positioned proximal of the first contact portion, and the first contact portion and the second contact portion are configured to move from respective positions in which the first contact portion and the second contact portion are spaced from one another to positions in which the first contact portion and the second contact portion contact one another to restrict relative axial movement of the first contact portion and the second contact portion. The sheath assembly comprises a dilator that includes a distal end and a tapered outer surface that tapers toward the distal end of the dilator so that an outer diameter of the dilator becomes smaller toward the distal end of the dilator. The dilator includes a lumen that communicates with an open end at the distal end of the dilator, wherein the guide wire is positionable in the lumen in the dilator.

BRIEF DESCRIPTION OF THE DRAWINGS

FIGS. 4A and 4B are cross-sectional views showing the distal end portion of the guide wire according to the embodiment. FIG. 4A shows a state in which a cover portion is contracted. FIG. 4B shows a state in which a force for extending the cover portion is applied.

FIG. 5A shows a state in which a puncture portion protrudes from the cover portion and punctures a foramen ovalis. FIG. 5B shows a state in which the puncture portion is accommodated in the cover portion.

FIG. 6A shows a first modification. FIG. 6B shows a second modification. FIG. 6C shows a third modification. FIG. 6D shows a fourth modification.

DETAILED DESCRIPTION

Figure 1:
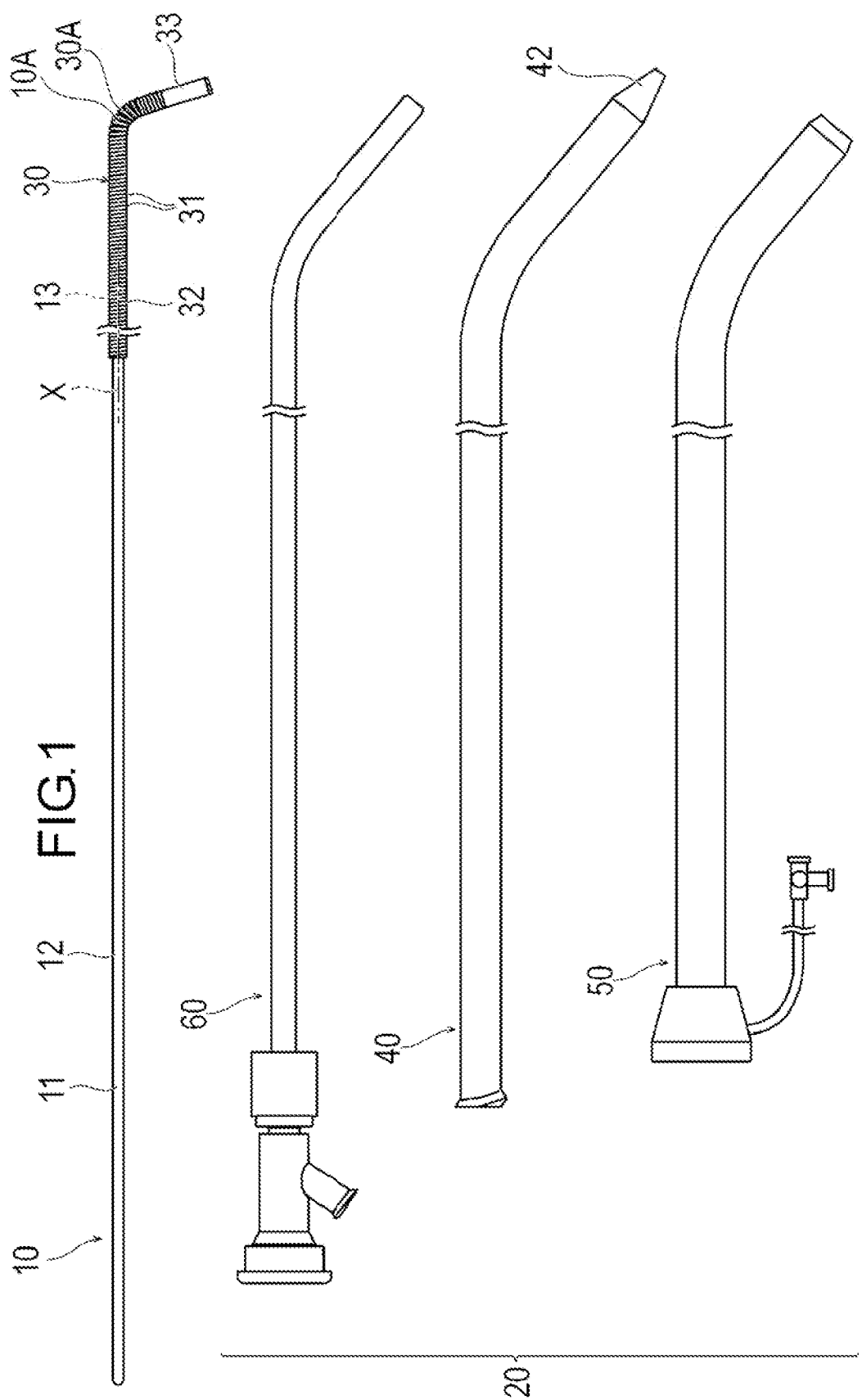
FIG. 1 is a plan view showing a guide wire and a sheath assembly according to an embodiment.

Set forth below with reference to the accompanying drawings is a detailed description of embodiments of a guide wire representing examples of the inventive guide wire disclosed here. For convenience of explanation, dimensions in the drawings may be exaggerated and may be different from actual dimensions. Further, in the present specification and the drawings, structural elements that have the same or substantially the same function are denoted with the same reference numerals, and a detailed explanation of these features will not be repeated. In the present specification, a side to be inserted into a lumen is referred to as a "distal end side", and a hand-side to be operated by a user or operator is referred to as a "proximal end side".

A guide wire 10 according to an embodiment of this disclosure has a puncture function, and is used to form a hole leading from a right atrium to a left atrium in a foramen ovalis O. The hole may be a cut. When the foramen ovalis O has the hole, an ablation catheter percutaneously inserted into a vena cava can be guided to the right atrium and then inserted into the left atrium through the hole to ablate the periphery of the pulmonary vein opening. That is, the guide wire 10 is used to form an access route for the ablation catheter in the foramen ovalis O.

As shown in FIG. 1, the guide wire 10 is used together with a sheath assembly 20 into which the guide wire 10 can be inserted. The sheath assembly 20 includes a reinforcing tube 60 into which the guide wire 10 is inserted, a dilator 40 into which the reinforcing tube 60 is inserted, and an outer sheath 50 into which the dilator 40 is inserted.

Figure 2:
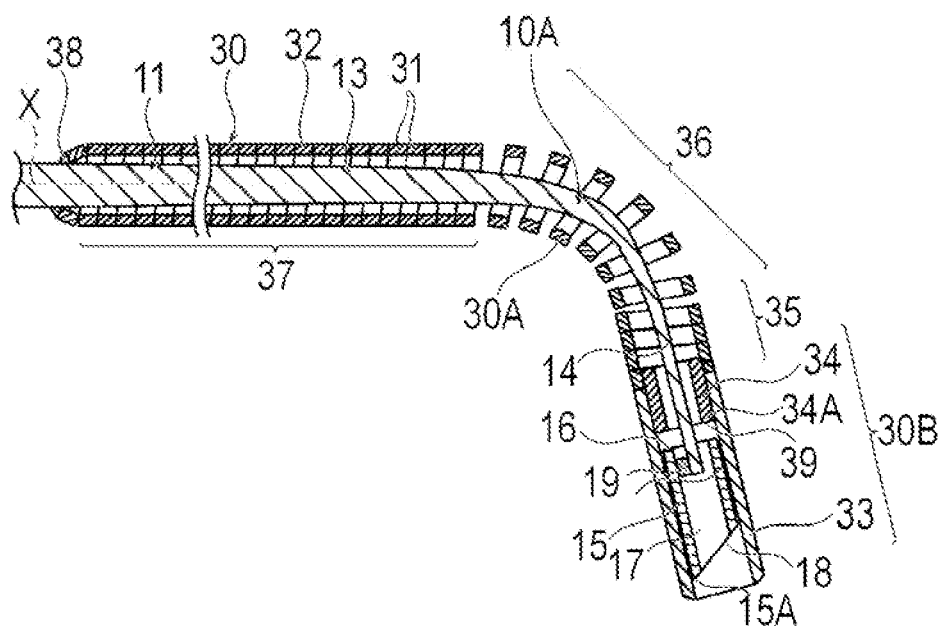
FIG. 2 is a cross-sectional view showing a distal end portion of the guide wire according to the embodiment.

The guide wire 10 is an elongated device that guides the sheath assembly 20 including the dilator 40 and the ablation catheter to a target position in a blood vessel. The guide wire 10 also has a function of puncturing the foramen ovalis O. As shown in FIGS. 1 and 2, the guide wire 10 includes a shaft portion 11 that is an elongated wire member, a puncture portion 15 including a sharp needle portion 15A, and a cover portion 30 that accommodates the puncture portion 15.

The guide wire 10 has a wire curve portion 10A whose axial center is bent at a portion where the cover portion 30 covers the shaft portion 11. The wire curve portion 10A is bent by fixing the unbent cover portion 30 to the bent shaft portion 11. Alternatively, the wire curve portion 10A may be bent by fixing the bent cover portion 30 to the unbent shaft portion 11. Alternatively, the wire curve portion 10A may be bent by fixing the bent cover portion 30 to the bent shaft portion 11.

The wire curve portion 10A is bent in a natural state in which an external force from gravity, a blood flow, or the like does not act. That is, the wire curve portion 10A is bent in the absence of any force applied to or acting on the wire curve portion 10A. The wire curve portion 10A may not be bent in the natural state when the wire curve portion 10A is bent in a use environment. For example, the wire curve portion 10A may be bent by an action of its own weight, or may be bent by receiving a force from a flow of blood. Since the guide wire 10 is flexible, even if the guide wire 10 is not bent in the natural state, the wire curve portion 10A can be formed in its bent shape by its own weight, the action of an external force from the blood flow, or the like.

The shaft portion 11 includes a shaft proximal end portion 12 located on a proximal end side, a shaft distal end portion 14 located on a distal end side, and a shaft decreased diameter portion 13 located between the shaft proximal end portion 12 and the shaft distal end portion 14. The shaft proximal end portion 12 is a portion located on the proximal end side and having a constant outer diameter. The shaft decreased diameter portion 13 is a portion that extends from the shaft proximal end portion 12 toward the distal end side and has an outer diameter reduced in a tapered shape. The outer diameter of the shaft decreased diameter portion 13 is reduced in the tapered shape, so that physical properties such as flexural rigidity are gradually changed along the axial direction. Therefore, the shaft decreased diameter portion 13 can prevent the occurrence of a kink or the like due to a rapid change in the physical properties. The flexural rigidity of the shaft decreased diameter portion 13 is gradually reduced along the axial direction. Therefore, the shaft portion 11 has high pushing performance and accessibility in a bent blood vessel. The shaft distal end portion 14 is a portion extending from the shaft decreased diameter portion 13 toward the distal end side and having a constant outer diameter. The outer diameter of the shaft distal end portion 14 is smaller than the outer diameter of the shaft proximal end portion 12. The outer diameter of the shaft distal end portion 14 may not be constant.

A constituent material for the shaft portion 11 preferably has flexibility and is hard to some extent. For example, metals such as stainless steel, tantalum, titanium, platinum, gold, and tungsten, shape memory alloys to which shape memory effects and superelasticity are imparted by heat treatment, polyolefins such as polyethylene and polypropylene, polyesters such as polyamide and polyethylene terephthalate, fluorine-based polymers such as PTFE (polytetrafluoroethylene) and ETFE (ethylene-tetrafluoroethylene copolymer), PEEK (polyether ether ketone), and polyimide can be suitably used. As the shape memory alloy, a Ni—Ti based alloy, a Cu—Al—Ni based alloy, a Cu—Zn—Al based alloy, or the like can be suitably used. The shaft portion 11 may include an X-ray contrast material. The X-ray contrast material is preferably formed of, for example, at least one metal or two or more alloys selected from a group formed of gold, platinum, iridium, tungsten, alloys thereof, and silver-palladium alloys.

A length of the shaft portion 11 in the axial direction is, for example, 300 mm to 5000 mm, preferably 1000 mm to 3000 mm, and more preferably 1500 mm to 2500 mm. The outer diameter of the shaft distal end portion 14 is, for example, 0.04 mm to 0.8 mm, preferably 0.08 mm to 0.4 mm, and more preferably 0.12 mm to 0.35 mm. The outer diameter of the shaft proximal end portion 12 is, for example, 0.3 mm to 1.0 mm, preferably 0.4 mm to 0.8 mm, and more preferably 0.7 mm to 0.8 mm.

The puncture portion 15 is a circular tube having the sharp needle portion 15A configured to pierce the biological tissue. The puncture portion 15 includes a through hole 17 penetrating from the proximal end side to the distal end side. The puncture portion 15 is fixed to the distal end portion of the shaft portion 11. The puncture portion 15 has an inclined surface 18 inclined with respect to a central axis at the distal end. The sharp needle portion 15A for puncturing the biological tissue is formed at the distal end of the inclined surface 18. The distal end of the shaft distal end portion 14 is disposed inside the puncture portion 15. The distal end of the shaft distal end portion 14 is fixed to an inner peripheral surface of the puncture portion 15 by a needle fixing portion 19 by welding, adhesion, or the like. The inner diameter of the puncture portion 15 is larger than the outer diameter of the shaft distal end portion 14. It is preferable that the axial center of the puncture portion 15 and the axial center of the shaft distal end portion 14 substantially coincide with each other. Alternatively, the axial center of the puncture portion 15 and the axial center of the shaft distal end portion 14 may not coincide with each other. A shape of the needle portion 15A is not particularly limited as long as the needle portion 15A can puncture biological tissue, and may be, for example, a conical shape, a knife-type flat plate, or a shovel-like curved plate. Therefore, the through hole 17 may not be formed in the puncture portion 15. A cross-sectional shape of the puncture portion 15 may not be circular. The puncture portion 15 may have a structure integrated with the shaft portion 11. The puncture portion 15 may be an electrode or the like capable of emitting energy such as current or heat. A first contact portion 16 that can come into contact with a second contact portion 39, which will be described later, is formed on a surface of the proximal end side of the puncture portion 15.

A length of the puncture portion 15 in the axial direction is preferably set such that the flexibility of the guide wire 10 in the blood vessel is not impaired. The length of the puncture portion 15 in the axial direction may be, for example, 2 mm to 10 mm, preferably 2 mm to 6 mm, and more preferably 2 mm to 4 mm. The outer diameter of the puncture portion 15 is, for example, 0.3 mm to 1.0 mm, preferably 0.4 mm to 0.8 mm, and more preferably 0.7 mm to 0.8 mm. The inner diameter of the puncture portion 15 is, for example, 0.1 mm to 0.9 mm, preferably 0.2 mm to 0.7 mm, and more preferably 0.3 mm to 0.5 mm. An inclination angle of the inclined surface 18 of the puncture portion 15 with respect to the central axis is appropriately set, and is, for example, 3 degrees to 45 degrees, preferably 5 degrees to 40 degrees, and more preferably 10 degrees to 35 degrees.

A constituent material from which the puncture portion 15 may be fabricated is preferably hard to some extent. For example, metals such as stainless steel, tantalum, titanium, platinum, gold, and tungsten, polyolefins such as polyethylene and polypropylene, polyesters such as polyamide and polyethylene terephthalate, fluorine-based polymers such as PTFE (polytetrafluoroethylene) and ETFE (ethylene-tetrafluoroethylene copolymer), PEEK (polyether ether ketone), and polyimide can be suitably used.

The cover portion 30 accommodates the puncture portion 15 in an exposable manner (i.e., the cover portion 30 accommodates the puncture portion 15 in a way allowing the puncture portion 15 to be exposed), and has a tubular shape as a whole. The cover portion 30 has an elastically deformable portion. Deformation includes both that the cover portion 30 can be contracted along a central axis X of the cover portion 30 and that the cover portion 30 can be moved between a state in which the central axis X of the cover portion 30 is bent and a state in which the central axis X of the cover portion 30 is linear. The cover portion 30 includes a coil portion 32 formed of a wire member 31 that draws a spiral, an accommodation tube 33 that is fixed to a distal end side of the coil portion 32, and a stopper 34 that is fixed to an inner side of a proximal portion of the accommodation tube 33. The coil portion 32 has an elastically deformable portion.

The accommodation tube 33 is a circular tube that slidably accommodates the puncture portion 15. A distal end surface of the accommodation tube 33 is curved (rounded) and smoothly formed. The accommodation tube 33 may be formed by joining together the wire member 31 that draws spiral lines (i.e., the wire member 31 that defines spiral windings). Although the wire member 31 forming the accommodation tube 33 preferably traces a spiral configuration without gaps between axially adjacent windings, gaps between axially adjacent windings may exist.

The stopper 34 is a member that restricts excessive extension of the cover portion 30 by coming into contact with the puncture portion 15. For example, the stopper 34 is a circular tube fitted and fixed to the inside of the proximal portion of the accommodation tube 33. The stopper 34 is located on the proximal end side of the puncture portion 15 inside the accommodation tube 33. The shaft portion 11 penetrates the inside of the stopper 34. That is, the shaft portion 11 is positioned inside the stopper 34. The inner diameter of the stopper 34 is smaller than the outer diameter of the puncture portion 15. Therefore, the puncture portion 15 cannot pass through an inner cavity of the stopper 34. The second contact portion 39 of the stopper 34 that can come into contact with the first contact portion 16 of the puncture portion 15 is formed on the surface on the distal end side of the stopper 34. The second contact portion 39 that can come into contact with the first contact portion 16 is formed in a stepped portion 34A whose inner diameter changes from the inner peripheral surface of the accommodation tube 33. The second contact portion may be formed at a portion where the inner diameter changes in a tapered shape from the inner peripheral surface of the accommodation tube 33. The second contact portion may be formed on a distal end surface of the coil portion 32.

A constituent material from which the accommodation tube 33 may be made is preferably hard to some extent. For example, metals such as stainless steel, tantalum, titanium, platinum, gold, and tungsten, polyolefins such as polyethylene and polypropylene, polyesters such as polyamide and polyethylene terephthalate, fluorine-based polymers such as PTFE (polytetrafluoroethylene) and ETFE (ethylene-tetrafluoroethylene copolymer), PEEK (polyether ether ketone), and polyimide can be suitably used.

The coil portion 32 is formed of one continuous wire member 31. Alternatively, the coil portion 32 may be formed of a plurality of wire members. The coil portion 32 has a substantially constant outer diameter and a substantially constant inner diameter along the central axis X of the spiral. The coil portion 32 includes a distal end dense pitch portion 35 located on the distal end side, a sparse pitch portion 36 located on the proximal end side with respect to the distal end dense pitch portion 35, and a proximal end dense pitch portion 37 located on the proximal end side with respect to the sparse pitch portion 36. The distal end dense pitch portion 35 and the proximal end dense pitch portion 37 have a pitch distance of the spiral shorter than that of the sparse pitch portion 36. The pitch distance is a movement distance in the axial direction when the spiral is wound 360 degrees in a circumferential direction. Therefore, the distal end dense pitch portion 35 and the proximal end dense pitch portion 37 hardly contract along the central axis X of the spiral. In the distal end dense pitch portion 35 and the proximal end dense pitch portion 37, the axially adjacent spiral windings of the wire member 31 may be in contact with each other without a gap, or may be separated from each other so that an axially gap or space exist between axially adjacent windings of the wire member. In the sparse pitch portion 36, the gap is formed between the adjacent wire members 31. Therefore, the sparse pitch portion 36 can contract or shorten along the central axis X of the spiral. A configuration of the coil portion 32 is not particularly limited as long as the coil portion 32 includes a portion that can contract along the central axis X of the spiral.

The proximal end of the coil portion 32 is fixed to the shaft portion 11 by a joint portion 38 made of solder, an adhesive, a material melted by welding, or the like. The joint portion 38 fills a step and a gap between the proximal end of the coil portion 32 and the shaft portion 11. The central axis X of the spiral of the coil portion 32 substantially coincides with the axial centers of the shaft proximal end portion 12, the shaft decreased diameter portion 13, and the shaft distal end portion 14.

The coil portion 32 is disposed at a position overlying or axially overlapping the wire curve portion 10A of the guide wire 10, thereby forming a curve portion 30A that is movable between a state in which the central axis X is bent and a state in which the central axis X is linear. The curve portion 30A is curved in one direction in the curved state. The central axis X of the spiral in the curve portion 30A may or may not coincide with the axial center of the shaft portion 11. The shaft portion 11 may or may not come into contact with the inner peripheral surface of the curve portion 30A.

A bending angle of the curve portion 30A is not particularly limited, and is preferably 45 degrees to 85 degrees, and more preferably 70 degrees to 85 degrees. By providing the curve portion 30A, when the guide wire 10 is pushed forward in a living body, the distal end of the guide wire 10 is less likely to abut on the biological tissue, and damage to the biological tissue can be prevented.

The cross-sectional shape of the wire member 31 forming the cover portion 30, which is orthogonal to an extending direction of the wire member 31, is circular. Accordingly, a spring constant of the coil portion 32 can be reduced. Therefore, the coil portion 32 can be easily deformed at the time of puncturing, and puncture resistance can be reduced. The cross-sectional shape of the wire member 31 forming the cover portion 30 may not be circular, and may be, for example, elliptical, rectangular, square, parallelogram, or trapezoidal. If the cross-sectional shape of the wire member 31 is rectangular or square, when the cover portion 30 contracts along the central axis X, the wire member 31 arranged along the central axis X comes into contact with a large area. Therefore, in the cover portion 30 contracted along the central axis X, a transmission force of the force in the direction along the central axis X is improved.

The cover portion 30 includes a distal end cover 30B that is not deformable along the central axis X, on the distal end side of a portion of the coil portion 32 that is deformable along the central axis X. In the present embodiment, the distal end cover 30B includes the accommodation tube 33 and the stopper 34. Alternatively, in the present embodiment, the distal end cover 30B may be constituted by the accommodation tube 33, the stopper 34, and a part of the wire member 31 fixed to the accommodation tube 33 or the stopper 34. The first contact portion 16 described above is located on the undeformable distal end cover 30B located on the distal end side of the deformable portion.

The length of the guide wire 10 is appropriately set, and is, for example, 300 mm to 5000 mm.

The coil portion 32 is formed by spirally winding the linear wire member 31. Alternatively, the coil portion 32 may be cut out from the circular tube by laser processing or the like.

A constituent material from which the coil portion 32 may be fabricated is preferably elastically deformable and hard to some extent. For example, a shape memory alloy to which a shape memory effect or superelasticity is imparted by heat treatment, a metal such as stainless steel, tantalum, titanium, platinum, gold, or tungsten, a polyolefin such as polyethylene or polypropylene, a polyester such as polyamide or polyethylene terephthalate, a fluorine-based polymer such as PTFE (polytetrafluoroethylene) or ETFE (ethylene-tetrafluoroethylene copolymer), PEEK (polyether ether ketone), or polyimide can be suitably used. As the shape memory alloy, a Ni—Ti based alloy, a Cu—Al—Ni based alloy, a Cu—Zn—Al based alloy, or the like can be suitably used. The coil portion 32 may include an X-ray contrast material. The X-ray contrast material is preferably formed of, for example, at least one metal or two or more alloys selected from a group formed of gold, platinum, iridium, tungsten, alloys thereof, and silver-palladium alloys. Since the coil portion 32 is formed in a spiral shape, unevenness is increased, and high ultrasound imaging properties can be obtained.

In general, the guide wire 10 has high flexibility while having a certain degree of rigidity so as not to damage a biological lumen into which the guidewire 10 is inserted and so as to be pushed forward in a curved biological lumen. Therefore, in the guide wire 10 according to the present embodiment, when the distal end portion of the cover portion 30 receives a force toward the proximal end side in a state in which deflection (deformation in the radial direction) is not restricted, any portion of the guide wire 10 is deflected, and the force escapes from the distal end portion of the cover portion 30 to another portion. Further, since the distal end portion of the guide wire 10 is bent, the force toward the proximal end side is less likely to act thereon, and a force that contracts the cover portion 30 toward the central axis X is less likely to act thereon. Therefore, even when the cover portion 30 receives the force toward the proximal end side at the distal end, a force necessary to contract the cover portion 30 toward the central axis X does not act on the cover portion 30. Therefore, the cover portion 30 is bent by receiving the force toward the proximal end side in a free deflection state, and maintains a state in which the needle portion 15A is accommodated.

Figures 5A, 5B:
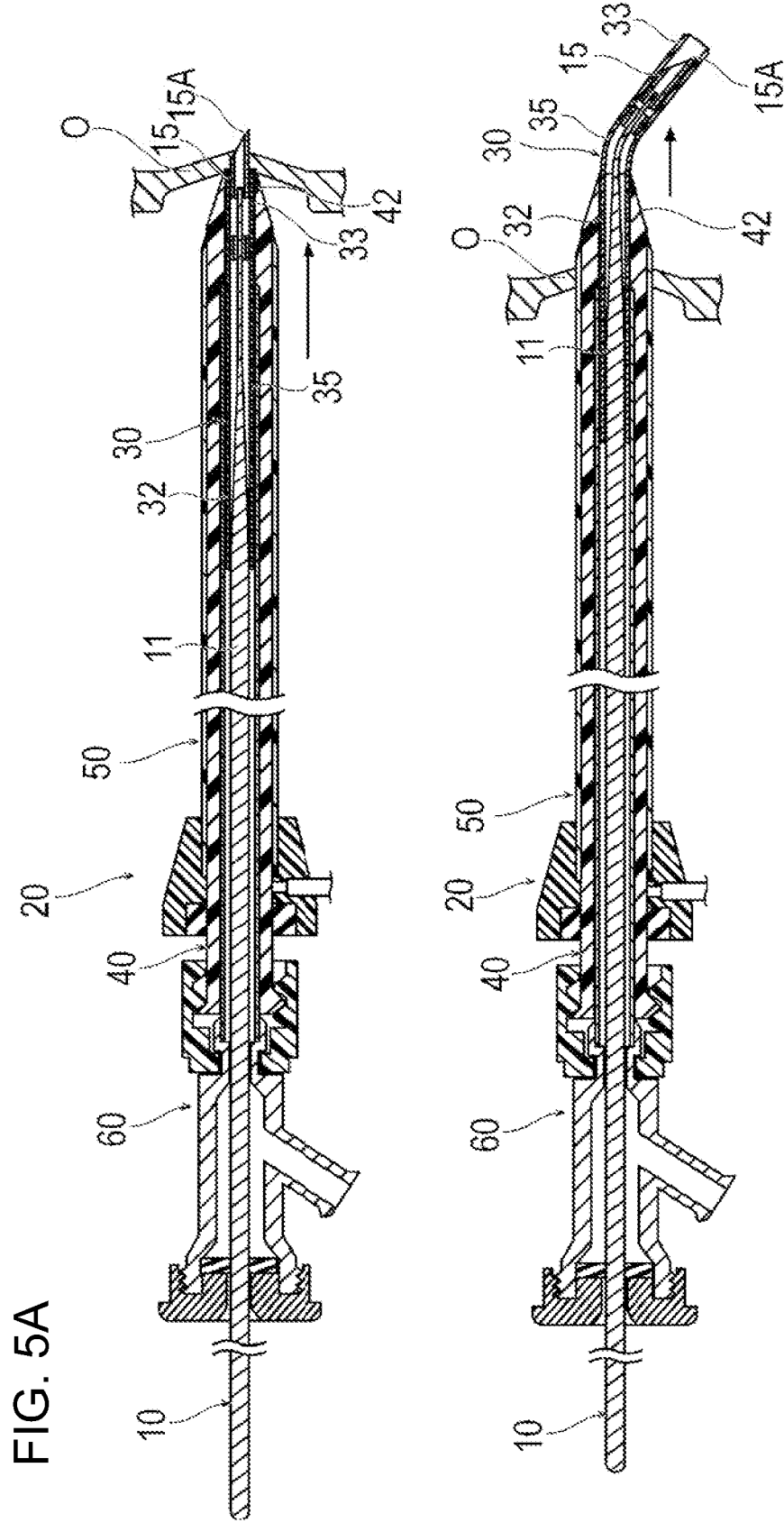
FIGS. 5A and 5B are cross-sectional views showing a state when puncture is performed with the guide wire.

As shown in FIGS. 1 and 5A, the reinforcing tube 60 used together with the guide wire 10 can receive the guide wire 10, and then reinforcing tube 60 (with the guide wire 10) is inserted into the dilator 40. In order to appropriately puncture the foramen ovalis O, it is necessary to provide the device with an appropriate angle and rigidity so as to appropriately face the foramen ovalis O in the right atrium. The reinforcing tube 60 can be inserted into the dilator 40 to increase the rigidity and angle of the device, and thereby ensure the device appropriately faces or is appropriately oriented relative to the foramen ovalis O in the right atrium.

The dilator 40 is used to widen the hole of the foramen ovalis O formed by the guide wire 10. The dilator 40 has a tapered outer portion 42 at a distal end portion thereof. The outer diameter of the tapered portion 42 is reduced toward the distal end side in a tapered shape. An inner cavity (lumen or through opening) of the dilator 40 opens at the end portion (distal end portion) of the tapered portion 42 where the outer diameter is the smallest. The reinforcing tube 60 is inserted into the dilator 40 from the opening on the proximal end side.

The dilator 40 is inserted into the outer sheath 50 from the opening on the proximal end side of the outer sheath 50. The outer sheath 50 can pass through the hole of the foramen ovalis O formed by the guide wire 10 together with the dilator 40. After the dilator 40 is removed, the inner cavity of the outer sheath 50 provides an access route of the ablation catheter.

Next, operation and effects of the guide wire 10 according to the present embodiment will be described.

As shown in FIG. 5A, the guide wire 10 is accommodated in an assembly including the outer sheath 50 and the dilator 40 in a state of being accommodated in the reinforcing tube 60. That is, the guide wire 10 is positioned in reinforcing tube 60, the combination of the guide wire 10 and the reinforcing tube 60 is positioned in the dilator 40, and the combination of the guide wire 10, the reinforcing tube 60 and the dilator 40 is positioned in the outer sheath 50. At this time, the distal end of the guide wire 10 is disposed between an opening portion on the distal end side of the dilator 40 (open distal end of the dilator 40) and an opening portion on the distal end side of the reinforcing tube 60 (open distal end of the (open distal end of the reinforcing tube 60). When the guide wire 10 moves in the reinforcing tube 60 and the dilator 40, the puncture portion 15 of the guide wire 10 is maintained in a state of being accommodated in the cover portion 30. Accordingly, when the guide wire 10 moves in the reinforcing tube 60 and the dilator 40, the puncture portion 15 is prevented from damaging the reinforcing tube 60 and the dilator 40, or the puncture portion 15 itself is prevented from being damaged.

Figure 3:
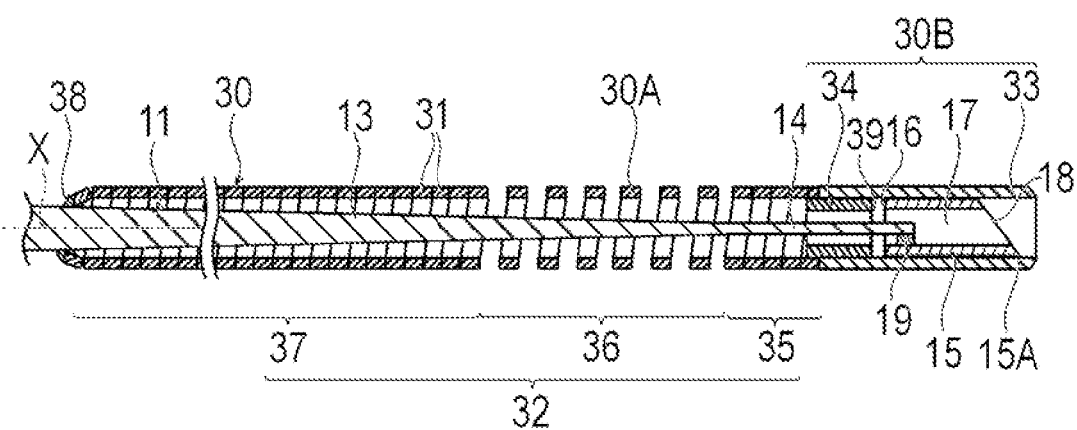
FIG. 3 is a cross-sectional view showing the distal end portion of the guide wire stretched linearly.

The guide wire 10 is pushed in a state in which the distal end of the dilator 40 abuts against the foramen ovalis O. That is, when the distal end of the dilator 40 abuts against or is in contact with the foramen ovalis O, the guide wire 10 is pushed in or moved axially forward. As shown in FIG. 3, the curve portion 30A of the cover portion 30 is linearly deformed inside the reinforcing tube 60.

When the guide wire 10 moves to the distal end side inside the reinforcing tube 60 and the dilator 40 (i.e., when the guide wire 10 moves in the distal direction relative to the reinforcing tube 60 and the dilator 40), the cover portion 30 located on the distal end side of the guide wire 10 comes into contact with the foramen ovalis O. Accordingly, the force toward the proximal end side acts on the distal end of the cover portion 30 located at the most distal end of the guide wire 10. The linearly deformed curve portion 30A changes from the state shown in FIG. 3 to the state shown in FIG. 4A by receiving the force toward the proximal end side. Accordingly, the curve portion 30A of the cover portion 30 elastically contracts along the central axis X and so the space between adjacent windings of the cover portion in the curve portion 30A are reduced.

When the coil portion 32 contracts along the central axis X by virtue of the guide wire 10 moving in the distal direction relative to the reinforcing tube 60 and the dilator 40, as shown in FIGS. 4A and 5A, the accommodation tube 33 located on the distal end side of the curve portion 30A moves toward the proximal end side with respect to the puncture portion 15. Accordingly, the needle portion 15A of the puncture portion 15 accommodated inside the accommodation tube 33 is exposed from the accommodation tube 33 to the distal end side. That is, the needle portion 15A of the puncture portion 15 is positioned distally beyond the distal end of the accommodation tube 33. Therefore, the guide wire 10 can form a hole in the foramen ovalis O by the puncture portion 15 exposed from the cover portion 30. After the puncture portion 15 passes through the foramen ovalis O and reaches the left atrium, the cover portion 30 passes through the formed hole. When the distal end of the cover portion 30 passes through the hole, as shown in FIGS.

3 and 5B, the coil portion 32 that is elastically contracted extends along the central axis X due to its own restoring force. Accordingly, the puncture portion 15 is once again accommodated in the accommodation tube 33 of the cover portion 30 and so the needle portion 15A of the puncture portion 15 is positioned proximal of the distal end of the accommodation tube 33. The wire curve portion 10A and the curve portion 30A are automatically restored to their original bent shape upon protruding from the dilator 40 or the biological tissue. Since the cover portion 30 accommodating the puncture portion 15 protrudes from the dilator 40, the cover portion 30 is not restricted from being deflected. Therefore, even when the force toward the proximal end side acts on the distal end of the cover portion 30 located at the most distal end of the guide wire 10, the cover portion 30 can be freely deflected without being contracted along the central axis X. Therefore, the puncture portion 15 in the left atrium does not protrude from the cover portion 30, and the state of being accommodated in the cover portion 30 is maintained. Therefore, it is possible to prevent the puncture portion 15 from erroneously puncturing an unintended position. Since the wire curve portion 10A is bent, the distal end of the guide wire 10 is less likely to abut on the biological tissue. Therefore, damage to the biological tissue can be prevented by the wire curve portion 10A.

For example, when the guide wire 10 is pulled out, the biological tissue may be caught by the sparse pitch portion 36 of the cover portion 30. In such a state, in the case of a guide wire that does not include the first contact portion 16 and the second contact portion 39, when a tensile force toward a proximal direction acts on the shaft portion 11, the shaft portion 11 moves in the proximal direction as shown in FIG. 4B. Meanwhile, the movement of the cover portion 30 toward the proximal direction is restricted by the biological tissue. Accordingly, the shaft portion 11 and the cover portion 30 move relative to each other in the axial direction. Therefore, the cover portion 30 may be plastically deformed. However, in the guide wire 10, when the tensile force toward the proximal direction is applied to the shaft portion 11 in a state where the biological tissue is caught on the distal end portion of the cover portion 30, and the shaft portion 11 moves in the proximal direction, the first contact portion 16 and the second contact portion 39 come into contact with each other. Accordingly, the shaft portion 11 and the cover portion 30 are restricted from moving relative to each other in the axial direction, so that plastic deformation of the cover portion 30 can be prevented. As a result, excessive extension of the extendable coil portion 32 located on the proximal end side of the distal end cover 30B is restricted. Therefore, it is possible to prevent the puncture portion 15 from being exposed to the outside due to the plastic deformation of the cover portion 30. The guide wire 10 passing through the foramen ovalis O can guide movement of the dilator 40 and the outer sheath 50 from the right atrium to the left atrium.

As described above, the guide wire 10 according to the present embodiment is the guide wire 10 for guiding a tubular elongated body (for example, the dilator 40) to be inserted into a living body. The guide wire 10 includes: the elongated shaft portion 11 that has flexibility; the puncture portion 15 that is disposed at a distal end portion of the shaft portion 11 and forms a hole in a biological tissue; and the cover portion 30 that is elastically deformable and covers the puncture portion 15. The cover portion 30 includes the sparse pitch portion 36 that has the wire member 31 wound in a spiral shape and is contractible along a central axis X of winding, and the distal end cover 30B that is located on a distal end side of the sparse pitch portion 36 and is capable of covering at least a part of the puncture portion 15. The puncture portion 15 includes the first contact portion 16. The distal end cover 30B includes the second contact portion 39 located on a proximal end side with respect to the first contact portion 16, and relative movement of the first contact portion 16 and the second contact portion 39 in the axial direction is restricted by the first contact portion 16 coming into contact with the second contact portion 39.

In the guide wire 10 constituted as described above, since the cover portion 30 covers the puncture portion 15, the erroneous puncture by the puncture portion 15 is prevented, and high safety is obtained. In addition, since the first contact portion 16 comes into contact with the second contact portion 39, relative movement of the first contact portion 16 and the second contact portion 39 in the axial direction is restricted, and extension of the cover portion 30 is restricted. Therefore, in the guide wire 10, the plastic deformation in an extension direction of the cover portion 30 covering the puncture portion 15 can be prevented, unintended exposure of the puncture portion 15 can be prevented, and the high safety can be obtained. Since the puncture portion 15 is normally covered with the cover portion 30, it is possible to prevent the puncture portion 15 from damaging other devices during operation or damage to the puncture portion.

The distal end cover 30B has the stepped portion 34A on the inner peripheral surface thereof that approaches the central axis X. The second contact portion 39 is located at the step portion 34A. The first contact portion 16 is formed at the proximal portion of the puncture portion 15. Accordingly, the second contact portion 39 of the stepped portion 34A of the distal end cover 30B is brought into contact with the first contact portion 16 of the puncture portion 15, and the excessive extension of the cover portion can be favorably restricted.

Further, the stepped portion 34A is formed on the inner peripheral surface of the distal end cover 30B over the entire circumference. Accordingly, the second contact portion 39 of the stepped portion 34A provided over the entire circumference of the distal end cover 30B can be reliably brought into contact with the first contact portion 16 of the puncture portion 15, and the excessive extension of the cover portion 30 can be favorably restricted.

When positions of the first contact portion 16 and the second contact portion 39 move away from each other, the puncture portion 15 protrudes from the cover portion 30. Therefore, the guide wire 10 can puncture the biological tissue with the puncture portion 15 by separating the positions of the first contact portion 16 and the second contact portion 39 from each other.

This disclosure is not limited to the embodiment described above, and various modifications can be made by those skilled in the art within a scope of the technical idea of this disclosure. For example, the stopper 34 may not be formed on the inner peripheral surface of the distal end cover 30B over the entire circumference. Therefore, the stopper 34 may not be a circular tube. For example, the stopper 34 may be a portion that protrudes inward in the radial direction from a part of the inner peripheral surface of the accommodation tube 33 in the circumferential direction. The stopper 34 and the accommodation tube 33 may have an integrated structure.

Figure 6A:
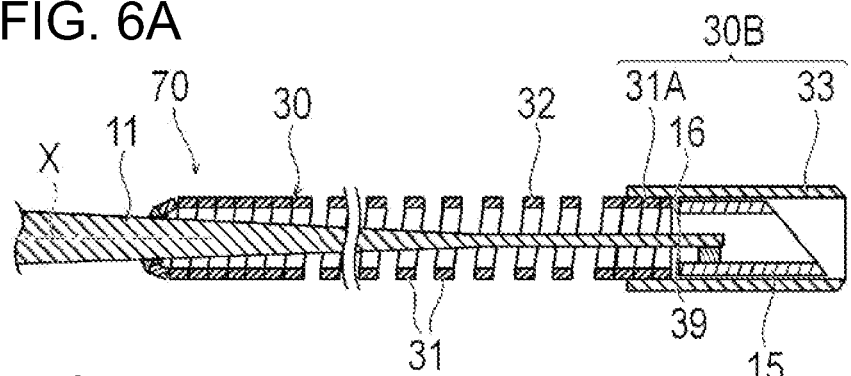
FIGS. 6A-6D are cross-sectional views showing a modification of the guide wire.

In addition, as in a guide wire 70 according to a first modification shown in FIG. 6A, a wire member fixing portion 31A which is a distal end portion of the spiral wire member 31 forming the coil portion 32 may be fixed to the inner peripheral surface of the proximal portion of the accommodation tube 33. The second contact portion 39 is located on a surface on the distal end side of the wire member fixing portion 31A. The first contact portion 16 is located on a surface on the proximal end side of the puncture portion 15.

As described above, the distal end cover 30B of the guide wire 70 according to the first modification includes the accommodation tube 33 that slidably accommodates the puncture portion 15, and the wire member fixing portion 31A that is continuously fixed to the inside of the accommodation tube 33 from the wire member 31 forming the coil portion 32 to the distal end side. The second contact portion 39 is located on the surface on the distal end side of the wire member fixing portion 31A. Accordingly, the second contact portion 39 located on the wire member fixing portion 31A continuous from the coil portion 32 is brought into contact with the first contact portion 16, and excessive extension of the cover portion 30 can be favorably restricted.

Figure 6B:
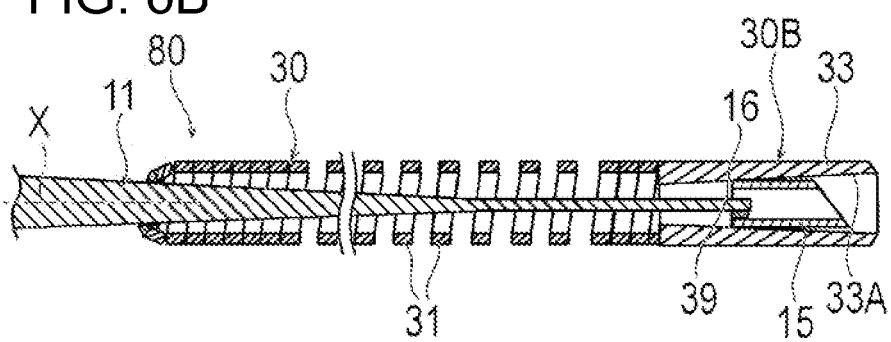

As in a guide wire 80 according to a second modification shown in FIG. 6B, the inner peripheral surface of the accommodation tube 33 may have an inclined portion 33A that approaches the central axis X toward the proximal end side. The second contact portion 39 is located at the inclined portion 33A. The first contact portion 16 is located at the proximal end of the puncture portion 15.

As described above, the distal end cover 30B of the guide wire 80 according to the second modification includes the accommodation tube 33 that slidably accommodates the puncture portion 15. The accommodation tube 33 includes the inclined portion 33A on the inner peripheral surface thereof that approaches the central axis X toward the proximal end side. The second contact portion 39 is located at the inclined portion 33A. Accordingly, the second contact portion 39 of the inclined portion 33A of the distal end cover 30B is brought into contact with the first contact portion 16, and excessive extension of the cover portion 30 can be favorably restricted.

Figure 6C:
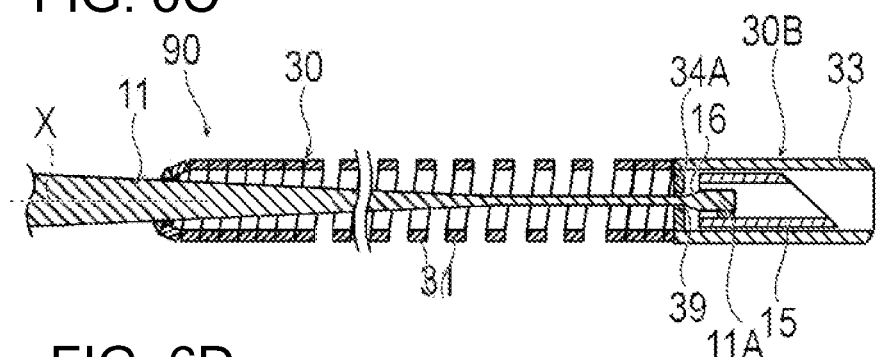

As in a guide wire 90 according to a third modification shown in FIG. 6C, the accommodation tube 33 may have a stepped portion 34A approaching the central axis X on the inner peripheral surface thereof. The second contact portion 39 may be located at the stepped portion 34A. The first contact portion 16 penetrates the stepped portion 34A and is located at a large-diameter portion (enlarged diameter portion) 11A of the shaft portion 11 located on the distal end side of the stepped portion 34A. An outer diameter of the large-diameter portion 11A is larger than an inner diameter of the inner peripheral surface of the stepped portion 34A. Accordingly, the large-diameter portion 11A cannot pass through the hole formed by the inner peripheral surface of the stepped portion 34A.

As described above, the distal end cover 30B of the guide wire 90 according to the third modification has the stepped portion 34A that approaches the central axis X on the inner peripheral surface. The second contact portion 39 is located at the stepped portion 34A. The first contact portion 16 is located at the large-diameter portion 11A that is disposed at the distal end portion of the shaft portion 11 and has an outer diameter larger than that of the proximal end side. Accordingly, the second contact portion 39 located at the stepped portion 34A of the distal end cover 30B is brought into contact with the first contact portion 16 of the shaft portion, and excessive extension of the cover portion 30 can be favorably restricted.

Figure 6D:
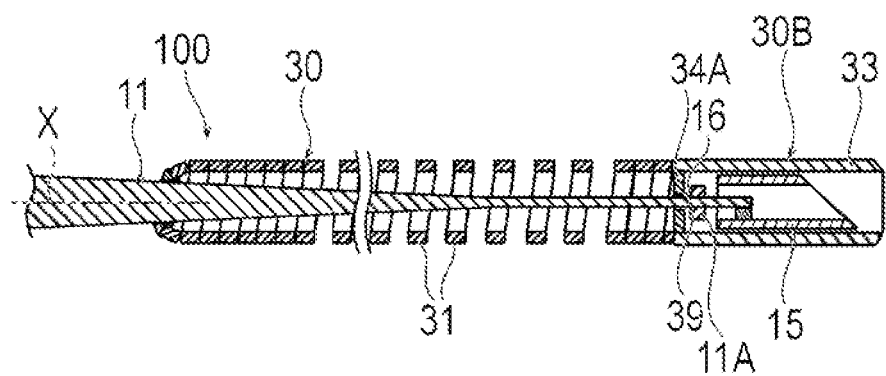

As in a guide wire 100 according to a fourth modification shown in FIG. 6D, the accommodation tube 33 may include a stepped portion 34A similarly to the third modification. The large-diameter portion 11A located at the distal end portion of the shaft portion 11 may be separated from the puncture portion 15 toward the proximal end side. Accordingly, when the second contact portion 39 located at the stepped portion 34A of the accommodation tube 33 comes into contact with the first contact portion 16 located at the large-diameter portion 11A, a force acting on the first contact portion 16 from the second contact portion 39 is not transmitted to the puncture portion 15. Therefore, the guide wire 100 can prevent the puncture portion 15 from falling off the shaft portion 11.

The detailed description above describes embodiments of a guide wire representing examples of the inventive guide wire disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A guide wire for guiding a dilator to be inserted into a living body, the guide wire comprising:
a flexible elongated shaft portion that includes a distal end portion;
a puncture portion fixed to the distal end portion of the elongated shaft portion so that the puncture portion moves together with the elongated shaft portion, the puncture portion including a distal end at which is located a sharp needle portion configured to puncture biological tissue in the living body to form a hole in the biological tissue;
a cover portion comprised of a sparse pitch portion and a distal end cover, the distal end cover being positioned distal of the sparse pitch portion, the sparse pitch portion being defined by a wire member that is spirally wound around a central axis of winding so that the wire member includes axially adjacent windings of the wire member, the axially adjacent windings of the wire member in the sparse pitch portion being axially spaced apart from one another so a gap exists between the axially adjacent windings allowing the sparse pitch portion to be axially contractible along the central axis of winding, the distal end cover covering at least a part of the puncture portion before a force is applied to the guide wire causing the sparse pitch portion to axially contract along the central axis of winding;
a first contact portion fixed to the shaft portion or the puncture portion;
a second contact portion on the distal end cover, the second contact portion being positioned proximal of the first contact portion;
the first contact portion and the second contact portion being configured to move from respective positions in which the first contact portion and the second contact portion are spaced from one another to positions in which the first contact portion and the second contact portion contact one another to restrict relative axial movement of the first contact portion and the second contact portion; and
the distal end cover including an accommodation tube and a stopper, the puncture portion being slidably accommodated in the accommodation tube, the stopper being positioned proximal of the puncture portion and being fixed inside the accommodation tube.

2. The guide wire according to claim 1, wherein the first contact portion is a proximal end of the puncture portion, the stopper including a through hole having an inner di mater, the inner diameter of the through hole in the stopper being smaller than an outer diameter of the proximal end of the puncture portion.

3. The guide wire according to claim 1, wherein the distal end cover includes a wire member fixing portion, the puncture portion being slidably accommodated in the accommodation tube, the wire member fixing portion being fixed to an inside of the accommodation tube, and the second contact portion being located at a distal end surface of the wire member fixing portion.

4. The guide wire according to claim 1, wherein the distal end cover includes a through-hole having an inner diameter that becomes gradually smaller toward a proximal direction so that an inner surface of the distal end cover is inclined.

5. The guide wire according to claim 1, wherein the distal end cover includes a through-hole having an inner peripheral surface, the inner peripheral surface of the distal end cover being stepped to define a stepped inner peripheral surface of the distal end cover, the second contact portion being located at the stepped inner peripheral surface, the distal end portion of the shaft portion including an enlarged diameter portion having an outer diameter larger than a portion of the shaft portion immediately proximal of the enlarged diameter portion, and the first contact portion being disposed at the enlarged diameter portion.

6. The guide wire according to claim 5, wherein the enlarged diameter portion is separated in a proximal direction from the puncture portion.

7. The guide wire according to claim 1, wherein the distal end cover includes a through-hole having an inner peripheral surface, the inner peripheral surface the distal end cover being stepped to define a stepped inner peripheral surface of the distal end cover, the second contact portion being located at the stepped inner peripheral surface of the distal end cover, and the first contact portion being located at a proximal portion of the puncture portion.

8. The guide wire according to claim 1, wherein the puncture portion is movable to a position distal of a distal end of the cover portion when the first contact portion and the second contact portion move away from each other so that the puncture portion is exposed outside the cover portion to puncture the biological tissue.

9. A guide wire for guiding a tubular elongated body to be inserted into a living body, the guide wire comprising:
a flexible elongated shaft portion that includes a distal end portion;
a puncture portion configured to form a hole in biological tissue in the living body, the puncture portion being at the distal end portion of the shaft portion;
an elastically deformable cover portion covering the puncture portion;
the cover portion including a sparse pitch portion defined by a wire member wound in a spiral shape around a central axis of winding and axially contractible along the central axis of winding, the cover portion also including a distal end cover located on a distal end side of the sparse pitch portion and configured to cover at least a part of the puncture portion;
the shaft portion or the puncture portion including a first contact portion;
the distal end cover including a second contact portion located on a proximal end side with respect to the first contact portion;
relative axial movement of the first contact portion and the second contact being restricted by the first contact portion coming into contact with the second contact portion;
the distal end cover including an accommodation tube in which is slidably accommodated the puncture portion, and a wire member fixing portion that is continuously fixed to an inside of the accommodation tube from the wire member that is wound in the spiral shape to a distal end side of the wire member fixing portion, and
the second contact portion being located on a surface on a distal end side of the wire member fixing portion.

10. The guide wire according to claim 9,
wherein the distal end cover has, on an inner peripheral surface thereof, an inclined portion that approaches the central axis toward the proximal end side, and
the second contact portion is located at the inclined portion of the distal end cover.

11. The guide wire according to claim 9,
wherein the distal end cover has, on an inner peripheral surface thereof, a stepped portion that approaches the central axis,
the second contact portion is located at the stepped portion,
the distal end portion of the shaft portion includes an enlarged diameter portion having an outer diameter larger than a portion of the shaft portion immediately proximal of the enlarged diameter portion, and
the first contact portion is disposed at the enlarged diameter portion.

12. The guide wire according to claim 11, wherein the enlarged diameter portion is separated in a proximal direction from the puncture portion.

13. The guide wire according to claim 9,
wherein the distal end cover has, on an inner peripheral surface thereof, a stepped portion that approaches the central axis,
the second contact portion is located at the stepped portion, and
the first contact portion is located at a proximal portion of the puncture portion.

14. The guide wire according to claim 11, wherein the stepped portion is formed on an inner peripheral surface of the distal end cover and extends over an entire circumference of the inner peripheral surface of the distal end cover.

15. The guide wire according to claim 9, wherein when the first contact portion and the second contact portion move in a direction away from each other, the puncture portion protrudes from the cover portion.

16. A guide wire in combination with a sheath assembly, the guide wire being configured to guide a part of the sheath assembly that is configured to be inserted into a living body, the guide wire comprising:
a flexible elongated shaft portion that includes a distal end portion;
a puncture portion fixed to the distal end portion of the elongated shaft portion so that the puncture portion moves together with the elongated shaft portion, the puncture portion including a distal end at which is located a sharp needle portion configured to puncture the biological tissue in the living body to form a hole in the biological tissue;
a cover portion comprised of a sparse pitch portion and a distal end cover, the distal end cover being positioned distal of the sparse pitch portion, the sparse pitch portion being defined by a plurality of axially adjacent windings that are axially spaced-apart from one another so the sparse pitch portion is axially contractible to reduce spacing between the axially adjacent windings that are axially spaced-apart, the distal end cover covering at least a part of the puncture portion before a force is applied to the guide wire causing the sparse pitch portion to axially contract;

a first contact portion fixed to the shaft portion or the puncture portion;

a second contact portion on the distal end cover, the second contact portion being positioned proximal of the first contact portion; and the first contact portion and the second contact portion being configured to move from respective positions in which the first contact portion and the second contact portion are spaced from one another to positions in which the first contact portion and the second contact portion contact one another to restrict relative axial movement of the first contact portion and the second contact portion; and the sheath assembly comprising a dilator, the dilator including a distal end and a tapered outer surface that tapers toward the distal end of the dilator so that an outer diameter of the dilator becomes smaller toward the distal end of the dilator, the dilator including a lumen that communicates with an open end at the distal end of the dilator, the guide wire being positionable in the lumen in the dilator.

17. The guide wire in combination with the sheath assembly according to claim 16, wherein the sheath assembly comprises a reinforcing tube, the guide wire being positioned in the reinforcing tube, the reinforcing tube being positionable in the lumen in the dilator.

18. The guide wire in combination with the sheath assembly according to claim 17, wherein the sheath assembly comprises an outer sheath, the dilator being positionable in the outer sheath while the reinforcing tube is positioned in the lumen in the dilator and while the guide wire is positioned in the reinforcing tube.

* * * * *